(12) United States Patent
Nakashiro

(10) Patent No.: US 6,498,122 B2
(45) Date of Patent: Dec. 24, 2002

(54) OLEFIN OXIDATION CATALYST AND PROCESS FOR ITS PRODUCTION

(75) Inventor: Katsumi Nakashiro, Yokkaichi (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 09/983,429

(22) Filed: Oct. 24, 2001

(65) Prior Publication Data

US 2002/0091291 A1 Jul. 11, 2002

(30) Foreign Application Priority Data

Oct. 25, 2000 (JP) .......................... 2000-324898
Oct. 25, 2000 (JP) .......................... 2000-324899

(51) Int. Cl.⁷ .................... B01J 23/48; C07D 301/10
(52) U.S. Cl. .................. 502/347; 502/243; 502/348; 549/534; 549/536
(58) Field of Search ............... 502/243, 347, 502/348; 549/534, 536

(56) References Cited

U.S. PATENT DOCUMENTS

| | | |
|---|---|---|
| 3,702,259 A | 11/1972 | Nielsen |
| 4,389,338 A | 6/1983 | Mitsuhata et al. |
| 4,555,501 A | 11/1985 | Armstrong |
| 4,690,913 A | 9/1987 | Nojiri et al. |
| 4,786,624 A | 11/1988 | Nojiri et al. |
| 4,864,042 A | 9/1989 | Armstrong |
| 5,705,661 A | 1/1998 | Iwakura et al. |

FOREIGN PATENT DOCUMENTS

| | | |
|---|---|---|
| EP | 0 389 389 | 9/1990 |
| EP | 0 764 464 | 3/1997 |
| EP | 0 788 838 | 8/1997 |
| WO | WO 00/15332 | 3/2000 |
| WO | WO 00/35893 | 6/2000 |

*Primary Examiner*—Sreeni Padmanabhan
(74) *Attorney, Agent, or Firm*—Oblon, Spivak, McClelland, Maier & Neustadt, P.C.

(57) ABSTRACT

An olefin oxidation catalyst comprising a carrier, and silver and an alkali metal supported thereon, wherein the content of organic substances is less than 0.1 wt %.

21 Claims, No Drawings

OLEFIN OXIDATION CATALYST AND PROCESS FOR ITS PRODUCTION

The present invention relates to a silver catalyst useful for the production of ethylene oxide by a gas phase oxidation of ethylene with oxygen, and a process for the preparation of the catalyst. Ethylene oxide is co-polymerized with an active hydrogen compound for a non-ionic surfactant, or it is converted into ethylene glycol or polyethylene glycol by an addition of water which is used as a starting material for a polyester or polyurethane type polymer or as an antifreezing agent for engines.

A silver catalyst has been used as a catalyst which is useful for industrially producing ethylene oxide by a gas phase oxidation of ethylene with oxygen. In order to efficiently produce ethylene oxide, a demand for improvement of such a silver catalyst has been strong, and it is desired to develop a catalyst having higher activity, higher selectivity and longer life. Accordingly, various proposals have been made for improvements in e.g. a method of supporting silver, and alkali metal or other additive components serving as a reaction accelerator of ethylene oxide production, and a carrier development.

For supporting silver on a carrier, it is considered preferable to use silver in the form of a complex solution by means of a complex-forming compound. As such a method, the following has been proposed. For example, there is a method of using an aqueous solution of a silver complex having monoethanolamine bonded to silver nitrate (JP-B-46-19606), a method of using an aqueous silver lactate solution (JP-B-47-20079), a method of using an ethanol solution of a silver carbonate/acetylacetone complex (JP-B-49-26603), a method of using an aqueous solution of a silver oxalate/ethylenediamine, monoethanolamine complex (JP-A-47-11467), a method of using a silver oxalate/ethylenediamine, 1,3-diaminopropane complex (JP-A-61-54242), or a method of using a toluene solution of silver neodecanoate (JP-A-60-244338).

In order to have silver supported on a carrier by means of such a complex-forming compound, it is common that a carrier is impregnated with a solution of a complex of silver, and then the impregnated carrier is heat-treated in a gas to decompose the silver complex. For such heat treatment, a method is employed which comprises depositing a layer of the impregnated carrier and permitting a heated gas to pass through the deposited layer. This method can be carried out by a batch system i.e. by a fixed bed system. However, for the production on an industrial scale, a method is commonly employed wherein the impregnated carrier is put on e.g. a belt and continuously passed through a heating apparatus.

As the gas for heating, an inert gas such as nitrogen, helium, argon or superheated steam, or a mixture of such an inert gas with air or oxygen, may be employed.

As an apparatus to be used for such heat treatment, a gas flow band dryer as disclosed, for example, in "Chemical Engineering Handbook (5th edition)" 1988, compiled by Society of Chemical Engineers, Japan, published by Maruzen Co., Ltd. on Mar. 18, 1988, p. 674–675, may be employed, and the impregnated carrier is heated by circulating a heated gas.

However, when a complex-forming compound is used to prepare a silver complex for silver impregnation on a carrier, the gas which is circulated in the heat treatment apparatus, will contain the complex-forming compound formed by the decomposition of the silver complex, or its decomposed products, and the solvent used to dissolve the complex. Accordingly, if the circulation of the gas is continued, they will be accumulated in a large amount in the gas, and the complex-forming agent or its decomposed products are likely to deposit on the catalyst, or the catalyst tends to be hardly completely dried.

Accordingly, it is necessary to discharge the gas passed through the deposited layer of the impregnated carrier out of the system in a certain proportion. However, if the amount of such discharge increases, the amount of a heated gas to be introduced afresh to supplement the discharged amount, will have to be increased, such being uneconomical. Accordingly, it is known to heat the impregnated carrier while discharging about 10 vol % of the gas passed through the deposited layer, taking into consideration the catalytic performance of the obtained catalyst.

In the catalyst obtained by such a method, organic substances which are considered to be the complex-forming compound and its decomposed products, remain in an amount of from 0.1 to 0.3 wt %. However, in the production of ethylene oxide by using the catalyst immediately after the preparation of the catalyst, they present no adverse effect, and ethylene oxide can be produced at a high selectivity.

The amount of the catalyst to be used in an installation for producing ethylene oxide on an industrial scale, is usually as much as a few tens tons. Accordingly, it is usual that the production of the catalyst is started a few months ahead of using the catalyst, and it takes at least a few months to produce the necessary amount of the catalyst, although it depends also on the capacity for the production of the catalyst. Further, in a case where the installation for the production of the catalyst is located far from the installation for the production of ethylene oxide, it may take a few months until the catalyst is delivered to the installation for the production of ethylene oxide. For such reasons, it is common that the catalyst is stored for about one year before it is actually used for the production of ethylene oxide.

However, there is a problem that if a catalyst which is capable of producing ethylene oxide at high selectivity when it is used within one year after the production, is used after being stored for a long period of time, the selectivity for ethylene oxide decreases by a few percent. Such a decrease in the selectivity gives a serious adverse effect from the viewpoint of the production cost of ethylene oxide on an industrial scale.

Accordingly, the object of the present invention is to provide a catalyst useful for the production of ethylene oxide, of which the performance will not decrease even when stored for a long period of time, and a process for the preparation of the catalyst. Thus, the catalyst invented shows a stable performance against storage.

The present inventor has conducted an extensive study to solve the problems of the storage degradation, and as a result, have found that the above problems are somehow attributable to an organic substance which results from a complex-forming compound used for supporting silver on the carrier and its decomposition product remaining in a trace amount in the catalyst in the conventional process for producing a catalyst for the production of ethylene oxide. On the basis of this discovery, the present invention has been accomplished.

Namely, according to the present invention, it is possible to produce a catalyst which maintains as high performance after long storage as that on its preparation, by impregnating a carrier with a solution having silver dissolved in the form of a complex with an organic compound and heating this impregnated carrier by a heated gas at a temperature of from 120 to 500° C., until the content of the organic compound will be less than 0.1 wt %, in the production of an olefin oxidation catalyst having at least silver and an alkali metal supported on a carrier, particularly a catalyst for producing ethylene oxide by ethylene oxidation.

Now, the present invention will be described in detail.

An oxidation catalyst for olefin, particularly ethylene, of the present invention is a catalyst having at least silver and an alkali metal supported on a carrier. As the alkali metal, cesium, or a combination of cesium and another alkali metal, such as lithium, is preferred.

As the carrier, a refractory such as alumina, silicon carbide, titania, zirconia or magnesia, may be mentioned. Among them, a refractory comprising α-alumina as a main component is preferred from the viewpoint of the performance of the final catalyst.

The carrier may be used, as it is, for supporting silver. However, it is preferred that an alkali metal is preliminarily supported thereon, and then silver is supported thereon. In general, a catalyst having a better performance can be obtained by supporting silver on a carrier on which an alkali metal is preliminarily supported. Most preferably, silver and an alkali metal are supported on a carrier on which an alkali metal is preliminarily supported. In order to have an alkali metal supported on a carrier, the carrier may be immersed in a solution containing an alkali metal, or sprayed with the solution, to have the carrier impregnated with the solution, and then, the impregnated carrier is heated to remove the solvent.

The alkali metal to be supported on a carrier includes, for example, cesium, lithium and sodium, preferably combination of cesium and lithium. Further, the heat treatment can be carried out at any temperature so far as the solvent of the impregnated solution can be evaporated and removed. However, industrially, it is preferably carried out at a temperature of from 120 to 500° C., particularly preferably from 120 to 250° C., by means of a heated gas. The heated gas may, for example, be an inert gas such as nitrogen, helium, argon or superheated steam, or a mixture of an inert gas with oxygen such as air. Among them, it is preferred to use superheated steam, whereby the distribution of the alkali metal in the finally obtainable catalyst will be uniform. In the present invention, silver, preferably silver and an alkali metal, are supported on a carrier, preferably a carrier having the above-mentioned alkali metal preliminarily supported thereon. As the alkali metal, the above-mentioned alkali metal to be preliminarily supported on the carrier may also be used, but it is preferred to use cesium at least from the viewpoint of the performance of the catalyst thereby obtainable. The alkali metal may be supported on the carrier by impregnating the carrier with a solution of an alkali metal hydroxide or an alkali metal salt, and then evaporating and removing the solvent. As such an alkali metal salt, a halide, a nitrate, an acetate, a carbonate, a hydrogencarbonate or a sulfate may be mentioned. The alkali metal is usually supported on the carrier together with silver. However, it may be supported before or after having silver supported on the carrier. Further, in addition to silver and the alkali metal, other metal elements such as an alkaline earth metal, rhenium, tungsten and molybdenum, may be supported on the carrier.

Silver may be supported by means of impregnating the carrier with a solution wherein silver is dissolved in the form of a complex and then by heating the impregnated carrier to decompose the complex. As is well known, the complex of silver can easily be prepared by reacting a silver compound with an organic compound as a complex-forming reagent. The silver compound may be a compound which is decomposable at a temperature of at most 500° C., preferably at most 300° C., more preferably at most 260° C., to deposit silver. As such a silver compound to be used for the formation of the complex, silver oxide, silver nitrate, silver carbonate, silver sulfate or various silver carboxylates such as silver oxalate, may, for example, be mentioned. Among them, silver oxalate is preferred, since the decomposition temperature is low.

The complex-forming compound may, for example, be ammonia, an amine compound or a compound having a carbonyl group or a carboxyl group. The amine compound may, for example, be a monoamine, a polyamine or an alkanolamine. The monoamine may, for example, be pyridine or an amine having from 1 to 6 carbon atoms. The polyamine may, for example, be ethylenediamine or 1,3-diaminopropane, and the alkanol amine may, for example, be ethanolamine. Among them, ethylenediamine and 1,3-diaminopropane are preferred from the viewpoint of the performance of the finally obtainable catalyst, and particularly preferred is a mixture of the two. Also, the compound having a carbonyl group may, for example, be acetylacetone, and the compound having a carboxyl group may, for example, be neodecanoic acid. As the solvent for the solution of a complex of silver with an organic compound, water is most preferred from the simplicity of the operation, but an aqueous solution having an alcohol added, or an organic solvent such as toluene, may also be used.

The method for impregnating the carrier with a solution having a complex of silver with an organic compound dissolved therein, may, for example, be a method of immersing the carrier in such a solution, or a method of spraying such a solution to the carrier.

The operation of heating the carrier impregnated with the complex of silver with the organic compound to decompose the complex and deposit silver, is carried out by contacting the impregnated carrier with a heated gas. The heating is carried out at a temperature of from 120 to 500° C. until the content of the organic compound in the resulting catalyst becomes less than 0.1 wt %. It is preferred to carry out the heating until the content of the organic compound in the catalyst becomes less than 0.05 wt %, particularly preferably less than 0.02 wt %. As the gas for the heating, an inert gas such as nitrogen, helium, argon or superheated steam, or a mixture of such an inert gas with oxygen such as air, may be employed. It is preferred to carry out the heating at a temperature of from 120 to 300° C., more preferably from 130 to 260° C., by using superheated steam. It is considered that when superheated steam is employed as the gas for heating, the distribution of silver and the alkali metal supported in the resulting catalyst will be uniform.

The heating of the impregnated carrier is carried out by a method wherein the impregnated carrier is continuously passed through a heating apparatus, i.e. a method wherein the impregnated carrier is continuously supplied to a heating apparatus, and while transporting it continuously in the apparatus from the inlet to the outlet, it is contacted with the heated gas. As the heating apparatus, a rotary kiln or the like may be employed, but it is preferred to employ a gas flow band dryer wherein the object to be dried is put on a gas flow type endless belt and transported in the dryer, while the heated gas is passed through the object to be dried from an upper or lower direction of the belt. Such a gas flow band dryer is disclosed, for example, in "Chemical Engineering Handbook (5th edition)" 1988, compiled by the Society of Chemical Engineers, Japan, and published by Maruzen Co., Ltd. on Mar. 18, 1988, p. 674–683.

The heated gas to be used for heating the impregnated carrier is recycled to increase the energy efficiency. Namely, the gas contacted to the impregnated carrier in the heating apparatus will be withdrawn from the drying apparatus, and introduced again into the drying apparatus after discharging a part of the withdrawn gas and, instead, supplementing a fresh heated gas from outside of the system, to suppress accumulation of the solvent or the complex-forming compound evolved from the impregnated carrier, or organic substances as the decomposition products of such solvent or complex-forming compound.

In the present invention, the heated gas is supplemented afresh from outside of the system in an amount of at least 10 m$^3$ per kg of the impregnated carrier supplied to the heating apparatus. If the amount of the fresh heated gas supplemented to the heated gas circulating in the heating apparatus, is small, organic substances will remain from 0.1 to 0.3 wt % in the resulting catalyst. If such a catalyst is used for producing ethylene oxide by oxidizing ethylene, after being stored for a long period of time, the selectivity for ethylene oxide will be lower by a few percent than immediately after the production. The reason why from 0.1 to 0.3 wt % of organic substances will remain in the resulting catalyst if the amount of the fresh heated gas supplemented to the circulating gas, is small, seems that organic substances will accumulate in the circulating gas, and a part thereof will be again adsorbed on the catalyst. However, if, in accordance with the present invention, a fresh heated gas is supplemented in an amount of at least 10 m$^3$, preferably at least 12 m$^3$ (in this specification, the volume of the gas is under the atmosphere wherein the impregnated carrier is present, and is not the volume as calculated as a standard state), per kg of the impregnated catalyst supplied to the heating apparatus, the content of organic substances in the resulting catalyst can be made to be at most 0.1 wt %. This is probably caused by the fact that the concentration of organic substances in the circulating gas is maintained at a low level. If such a catalyst having a low content of organic substances, is used for the production of ethylene oxide after being stored for a long period of time, the decrease in the selectivity for ethylene oxide, is small. In a preferred embodiment of the present invention, the fresh heated gas is supplemented to the circulating gas so that the content of organic substances in the resulting catalyst will be at most 0.05 wt %, particularly preferably at most 0.02 wt %.

For example, in a case where the impregnated carrier is heated in the above-mentioned gas flow band dryer to produce a catalyst, it is common to employ a gas flow type belt on which the impregnated carrier is deposited and which has a width of at least 25 cm and a length of at least 1 m, and to supply the impregnated carrier in an amount of at least 15 kg per hour. In a case where the impregnated carrier is supplied to the heating apparatus in an amount of 15 kg per hour, the fresh heated gas to be supplemented, is required to be at least 150 m$^3$, preferably at least 180 m$^3$, per hour. Further, in such a case, if the amount of the fresh heated gas to be supplemented is set to be 150 m$^3$/hr and 10% of the circulating gas is replaced by the fresh heated gas, the amount of gas to be passed through the deposited layer of the impregnated carrier on the gas flow type belt may be set to be 1,500 m$^3$/hr, and 150 m$^3$/hr thereof i.e. 10% thereof, may be discharged out of the apparatus, and to the remaining 1,350 m$^3$/hr, 150 m$^3$/hr of the fresh heated gas is supplemented, so that 1,500 m$^3$/hr of the gas will be again passed through the deposited layer of the impregnated carrier on the gas flow type belt. In such a case, the linear velocity of the circulating gas passing though the deposited layer of the impregnated carrier will be about 1.7 m/sec. When superheated steam is employed as the heated gas, the gas linear velocity passing through the deposited layer of the impregnated carrier is preferably from 0.3 to 5 m/sec from the viewpoint of the performance of the resulting catalyst. Further, the time required for the heat treatment is usually from 1 minute to 3 hours, preferably from 3 to 30 minutes. Namely, it is preferred to adjust the amount of the impregnated carrier to be supplied to the apparatus, the temperature of the superheated steam, the flow rate, etc., so that the impregnated carrier will pass through the heating apparatus within this period of time.

As another method, heating of the impregnated carrier may be carried out in two stages i.e. in the first and later stages. In the first stage, the majority of organic substances in the impregnated carrier is removed, and in the later stage, the remaining organic substances will be reduced to a level of less than 0.1 wt % by a gas flow comprising the fresh heated gas as a main component. In such a case, in the first stage, the gas in the heating apparatus is circulated, so that the consumption of the energy required for the heating of the impregnated carrier is reduced. When the gas is circulated while it is contacted with the impregnated carrier, the gas temperature decreases, and various gases evolved from the impregnated carrier will accumulate in the circulating gas. Accordingly, it is common to a heating apparatus provided in the circulation path of the gas to heat the circulating gas, and discharge a part of the circulating gas out of the system, and instead, supplement a fresh heated gas, so that the temperature of the circulating gas will be maintained constant. In a case where accumulation of the gas generated from the impregnated carrier in a high concentration, is not problematic, the amount of the fresh heated gas to be supplemented, can be reduced.

The majority of the contained organic substances on the carrier is removed by the heating in the first stage, then the carrier is heated in the later stage until the content of organic substances will be less than 0.1 wt %. It is preferred to carry out the heating until the content of organic substances will be less than 0.05 wt %, more preferably less than 0.02 wt %. The heating in the later stage is carried out by a heated gas comprising the freshly supplemented gas as a main component, so as to avoid a possibility that the gas evolved from the impregnated carrier will be accumulated in the heated gas and will hinder the removal of organic substances from the impregnated carrier. Most simply, the later stage heating is carried out solely by the fresh heated gas without circulating the gas. In a case where circulation of the gas is carried out, at least 90% of the circulating gas is replaced with the fresh supplemented gas. For example, the interior of the above-mentioned gas flow band dryer is divided into a first stage heating zone and a later stage heating zone, so that a gas flow is controlled independently in each zone. In the first heating zone, circulation of the gas is carried out by discharging from 5 to 30% of the heated gas passed through the deposited layer of the impregnated carrier on the gas flow type belt and instead, supplementing the same amount of a fresh gas, and in the later heating zone, the heated gas passed through the deposited layer of the impregnated carrier may be discharge totally, or at least 90% thereof may be discharged out of the system and instead, supplementing the same amount of a fresh gas. The gas discharged from the later stage heating zone has a temperature not substantially lowered and does not substantially contain the gas evolved from the impregnated carrier. Accordingly, this gas may be supplied to the first stage drying zone. The later stage heating is carried out usually for at least 5 minutes. In order to save the consumption of energy in the later stage heating, the later stage heating is preferably within 20 minutes.

In the present invention, the analysis of the content of organic substances in the catalyst is carried out by a method (TG-DTA) wherein a thermogravimetric measurement (TG) and a differential thermal analysis (DTA) are used in combination.

The method for the TG-DTA measurement is disclosed in "Fourth Edition of Experimental Chemistry Course 4; Heat•Pressure", compiled by the Chemical Society of Japan (1992), published by Maruzen Co., Ltd., on Feb. 5, 1992, p. 57–77. In the present invention, when the catalyst is subjected to the TG-DTA measurement in a stream of air, a heat generation and a weight loss which are considered to be attributable to combustion of organic substances contained in the catalyst and decomposition products thereof, are observed simultaneously during the period of an increasing temperature from about 225° C. to 275° C., and the content of organic substances in the catalyst is calculated from this weight loss. The catalyst obtained by the process of the present invention is useful as a catalyst for oxidation of an olefin, particularly for the production of ethylene oxide from ethylene. The production of ethylene oxide from ethylene by this catalyst, can be carried out by mean of a conventional method.

As a starting material gas for the reaction, a gas mixture comprising from 1 to 40 vol % of ethylene and from 1 to 20 vol % of oxygen, is employed, and a certain proportion, such as from 1 to 70 vol %, of a diluting agent such as methane or nitrogen gas, may usually be incorporated. As an oxygen source, air or industrial oxygen is used. Further, as a reaction modifier, e.g. a halogenated hydrocarbon may be added to the starting material gas in an amount of from about 0.1 to 50 vol ppm, whereby formation of hot spots in the catalyst can be prevented, and the performance, particularly the selectivity, of the catalyst can be substantially improved. The flow rate of the starting material gas for the reaction is usually from 1,000 to 10,000 $h^{-1}$ as calculated on a GHSV basis. Here, GHSV is defined by a gas flow rate at 0° C. under atmospheric pressure, per unit volume of the catalyst. The reaction can be carried out under a pressure of from 0.1 to 4 MPa (from 0 to 39 kg/cm$^2$G) at a temperature of from 180 to 350° C., preferably from 200 to 300° C.

Now, the present invention will be described in further detail with reference to Examples and Comparative Examples. However, it should be understood that the present invention is by no means restricted to such specific Examples. The contents of silver, cesium, lithium, sodium and barium in the catalysts used in Examples and Comparative Examples were measured by a chemical analysis. TG-DTA of the catalyst was performed with ca. 15 mg of a sample heated at a programmed temperature of 10° C./h under air flow of 50 ml/min.

EXAMPLE 1

Preparation of Impregnated Carrier 50 kg of an α-alumina carrier (surface area: 1.04 m$^2$/g, water absorption: 32.3%, average pore diameter: 1.4 μm, silica content: 3.0 wt %, ring shape having an outer diameter of 8 mm, an inner diameter of 3 mm and a height of 8 mm) was immersed in 100 l of an aqueous solution having 939 g of lithium carbonate (Li$_2$CO$_3$) and 86.5 g of cesium carbonate (CS$_2$CO$_3$) dissolved therein. By filtration, the carrier was collected. Then, superheated steam of 150° C. was passed through the deposit of the obtained impregnated carrier at a linear velocity of 2 m/sec for 20 minutes to obtain a carrier having lithium and cesium supported thereon. The lithium content in the carrier was 568 ppm by weight, and the cesium content was 227 ppm by weight.

Then, a solution having 49.0 kg of silver nitrate (AgNO$_3$) dissolved in 60 l of water and a solution having 6.40 kg of potassium oxalate (K$_2$C$_2$O$_4$.H$_2$O) dissolved in 60 l of water, were gradually mixed while heating to 60° C. in a water bath, to obtain white precipitate of silver oxalate. By filtration, the precipitate was collected, and washed with distilled water. 11.9 kg of silver oxalate (AgC$_2$O$_4$, water content: 19.5%) thus obtained was gradually added to an mixed amine aqueous solution comprising 3.44 kg of ethylenediamine, 943 g of 1,3-diaminopropane and 4 l of water and dissolved to obtain a silver amine complex solution.

To this silver amine complex solution, an aqueous solution comprising 11.4 g of cesium chloride (CsCl), 19.9 g of cesium nitrate (CsNO$_3$), 6.55 g of barium hydroxide octahydrate (Ba(OH)$_2$.8H$_2$O) and 417 ml of water, was added, and 1.73 l of water was further added.

Into an evaporator, 50 kg of the α-alumina carrier having lithium and cesium supported thereon, prepared as described above, and the silver amine complex solution containing cesium and barium, were put and held at 40° C. under reduced pressure, to obtain an impregnated carrier.

Heat Treatment of the Impregnated Carrier

This impregnated carrier was subjected to heat treatment by a continuous heating apparatus capable of supplying and discharging a gas. As the continuous heating apparatus, a gas flow band dryer as disclosed in FIG. 14 •23 on page 674 of "Chemical Engineering Handbook (5th edition)" 1988, complied by the Society of Chemical Engineers, Japan, and published by Maruzen Co., Ltd. on Mar. 18, 1988, was used. The size of the apparatus was such that the width was about 1 m, the length about 2 m and the height about 3 m, and the band surface through which the heated gas passes in the apparatus had a width of 25 cm and a length of 90 cm. As the heated gas, superheated steam of 200° C. was used, and this steam was contacted with the impregnated carrier placed on the band, at a linear velocity of 2 m/sec. The amount of the impregnated carrier introduced into the apparatus was 15 kg/hr, and the period passed through the apparatus was 20 minutes. The superheated steam was recycled, and at the time of recycling, about 10% of the gas was discharged out of the system, and the same amount of fresh superheated steam was supplemented. The amount of the supplemented superheated steam was 160 m$^3$/hr. Accordingly, the amount of superheated steam supplemented per kg of the amount of the impregnated carrier introduced, was 10.7 m$^3$. The contents of silver (Ag), cesium (Ce), lithium (Li) and barium (Ba) in the obtained catalyst, were 12 wt %, 590 ppm by weight, 470 ppm by weight and 50 ppm by weight, respectively. Further, the content of organic substances in the catalyst was less than 0.1 wt %. This catalyst was put into a bag made of a polyethylene sheet having a thickness of 0.1 mm, sealed and stored in a room.

Evaluation of the Performance of the Catalyst

Each of the catalysts stored for a period of 1 month, 8 months and 18 months, was pulverized to from 6 to 10 mesh, and 3 ml thereof was filled in a reaction tube made of stainless steel with an inner diameter of 7.5 mm. Into this reaction tube, a starting material gas for reaction (ethylene: 30 vol %, oxygen: 8.5 vol %, vinyl chloride: 1.5 ppm, carbon dioxide: 6.0 vol %, the rest being nitrogen) was permitted to pass through at a GHSV of 4,300 hr$^{-1}$ under a pressure of 0.8 MPa (7 kg/cm$^2$G) to carry out the reaction. The catalytic activity and the selectivity for ethylene oxide upon expiration of 1 week after initiation of the reaction, are shown in Table 1. Here, the catalytic activity is the reaction temperature (° C.) when the conversion of oxygen becomes 40%, and the selectivity is a ethylene selectivity for ethylene oxide, on 40% oxygen converted.

COMPARATIVE EXAMPLE 1

A catalyst was prepared in the same manner as in Example 1 except that in Example 1, at the time of the heat treatment of the impregnated carrier, the amount of the impregnated carrier introduced, was changed to 50 kg/hr. Accordingly, the amount of superheated steam supplemented per kg of the impregnated carrier was 3.2 m³. The content of organic substances in this catalyst was 0.2 wt %. The performance of this catalyst was evaluated in the same manner as in Example 1, and the results are shown in Table 1.

COMPARATIVE EXAMPLE 2

A catalyst was prepared in the same manner as in Example 1 except that in Example 1, at the time of the heat treatment of the impregnated carrier, the amount of the impregnated carrier introduced was changed to 25 kg/hr. Accordingly, the amount of superheated steam supplemented per kg of the impregnated carrier introduced, was 6.4 m³. The content of organic substances in this catalyst was 0.2 wt %. The performance of this catalyst was evaluated in the same manner as in Example 1, and the results are shown in Table 1.

COMPARATIVE EXAMPLE 3

A catalyst was prepared in the same manner as in Example 1 except that in Example 1, at the time of the heat treatment of the impregnated carrier, the amount of the impregnated carrier introduced was changed to 50 kg/hr, and the amount of superheated steam supplemented was changed to 250 m³/hr (15% of the circulating gas was discharged out of the system). Accordingly, the amount of superheated steam supplemented per kg of the impregnated carrier introduced, was 5 m³. The content of organic substances in this catalyst was 0.2 wt %. Further, the performance of this catalyst was evaluated in the same manner as in Example 1, and the results are shown in Table 1.

EXAMPLE 2

An impregnated carrier was prepared in the same manner as in Example 1 except that in Example 1, instead of immersing the α-alumina carrier in a solution containing lithium carbonate and cesium carbonate, the carrier was immersed in 100 l of an aqueous solution having 1.62 kg of sodium carbonate ($Na_2CO_3$) dissolved therein.

This impregnated carrier was subjected to heat treatment in the same manner as in Example 1 to obtain a catalyst. The amount of superheated steam supplemented per kg of the impregnated carrier introduced into the gas flow band dryer, was 10.7 m³. The amounts of silver (Ag), cesium (Cs), sodium (Na) and barium (Ba) supported on the obtained catalyst, were 12 wt %, 400 ppm by weight, 0.2 wt % and 50 ppm by weight, respectively.

The content of organic substances in this catalyst was less than 0.1 wt %. Further, the performance of this catalyst was evaluated in the same manner as in Example 1, and the results are shown in Table 1.

COMPARATIVE EXAMPLE 4

A catalyst was prepared in the same manner as in Example 2 except that in Example 2, the amount of the impregnated carrier introduced into the gas flow band dryer at the time of the heat treatment of the impregnated carrier, was changed to 50 kg/hr. The amount of superheated steam supplemented per kg of the amount of the impregnated carrier introduced, was 3.2 m³. The content of organic substances in this catalyst was 0.2 wt %. Further, the performance of this catalyst was evaluated in the same manner as in Example 1, and the results are shown in Table 1.

EXAMPLE 3

The impregnated carrier prepared in the same manner as in Example 1, was subjected to heat treatment by a continuous heating apparatus comprising a first heating zone and a later heating zone. This continuous heating apparatus was the same gas flow band dryer having a width of about 1 m, a length of about 2 m and a height of about 3 m, as used in Example 1, but the interior of the apparatus was divided by a partition plate into a first stage heating zone and a later stage heating zone. The band surface through which the heated gas was permitted to pass, had a width of 25 cm and a length of 115 cm. The first stage heating zone was 90 cm, and the later stage heating zone was 25 cm. As the heated gas, superheated steam of 200° C. was used, and this steam was contacted with the impregnated carrier deposited on the band at a linear velocity of 2 m/sec in both zones. The amount of the impregnated carrier introduced into the apparatus was 50 kg/hr, and it was permitted to pass through the apparatus in about 26 minutes (the first stage: 20 minutes, the later stage: 5.6 minutes). In the first stage heating zone, superheated steam was contacted with the impregnated carrier deposited on the band at a rate of 1,600 m³/hr, and 1,440 m³/hr corresponding to 90% thereof was recycled, while 160 m³/hr was discharged out of the system, and the same amount of superheated steam was supplemented. On the other hand, in the later stage heating zone, the gas was discharged in the entire amount out of the system without being recycled.

The content of organic substances in this catalyst was less than 0.1 wt %.

The amounts of silver (Ag), cesium (Cs), lithium (Li) and barium (Ba) supported on this catalyst, were 12 wt %, 590 ppm by weight, 470 ppm by weight and 50 ppm by weight, respectively, and were the same as in Example 1. The performance of this catalyst was evaluated in the same manner as in Example 1, and the results are shown in Table 1.

EXAMPLE 4

A catalyst was prepared in the same manner as in Example 3 except that in Example 3, the time in which the impregnated carrier was permitted to pass through the apparatus, was changed to about 77 minutes (the first stage: 60 minutes, the later stage: 16.8 minutes). The content of organic substances in this catalyst was less than 0.1 wt %. The performance of this catalyst was evaluated in the same manner as in Example 1, and the results are shown in Table 1.

EXAMPLE 5

A catalyst was prepared in the same manner as in Example 3 except that in Example 3, 1,150 m³/hr of the gas in the first stage heating zone was recycled, while 450 m³/hr was discharged out of the system, and instead, the same amount of superheated steam discharged from the later stage heating zone, was supplemented.

The content of organic substances in the catalyst was less than 0.1 wt %. The performance of this catalyst was evaluated in the same manner as in Example 1, and the results are shown in Table 1.

COMPARATIVE EXAMPLE 5

A catalyst was prepared in the same manner as in Example 3 except that in Example 3, the partition plate in the interior of the apparatus was taken out, and 1,600 m³/hr of superheated steam was contacted with the impregnated carrier deposited on the band, and 1,440 m³/hr thereof was recycled, while 160 m³/hr was discharged out of the system, and the same amount of superheated steam was supplemented. The content of organic substances in this catalyst was 0.2 wt %. The performance of this catalyst was evaluated in the same manner as in Example 1, and the results are shown in Table 1.

COMPARATIVE EXAMPLE 6

A catalyst was prepared in the same manner as in Example 3 except that in Example 3, 85% of the gas in the later stage heating zone was recycled, while 15% thereof was discharged and instead, the same amount of superheated steam was supplemented.

The content of organic substances in this catalyst was 0.2 wt %. The performance of this catalyst was evaluated in the same manner as in Example 1, and the results are shown in Table 1.

EXAMPLE 6

An impregnated carrier was prepared in the same manner as in Example 2. It was subjected to heat treatment in the same manner as in Example 3 to obtain a catalyst. The amounts of silver (Ag), cesium (Cs), sodium (Na) and barium (Ba) supported on the obtained catalyst, were 12 wt %, 400 ppm by weight, 0.2 wt % and 50 ppm by weight, respectively, and were the same as in Example 2. Further, the content of organic substances in this catalyst was less than 0.1 wt %. The performance of this catalyst was evaluated in the same manner as in Example 1, and the results are shown in Table 1.

COMPARATIVE EXAMPLE 7

A catalyst was prepared in the same manner as in Example 2 except that the impregnated carrier prepared, was subjected to heat treatment in the same manner as in Comparative Example 5.

The content of organic substances in this catalyst was 0.2 wt %. The performance of this catalyst was evaluated in the same manner as in Example 1, and the results are shown in Table 1.

TABLE 1

|  | Within 1 month | | 8 months later | | 18 months later | |
| --- | --- | --- | --- | --- | --- | --- |
|  | Activity (°C.) | Selectivity (%) | Activity (°C.) | Selectivity (%) | Activity (°C.) | Selectivity (%) |
| Ex. 1 | 225 | 81.5 | 225 | 81.5 | 225 | 81.5 |
| Comp. Ex. 1 | 225 | 81.5 | 226 | 80.2 | 217 | 76.9 |
| Comp. Ex. 2 | 225 | 81.5 | 225 | 80.5 | 219 | 78.1 |
| Comp. Ex. 3 | 225 | 81.5 | 226 | 80.3 | 218 | 77.1 |
| Ex. 2 | 228 | 80.8 | 228 | 80.8 | 228 | 80.8 |
| Comp. Ex. 4 | 228 | 80.8 | — | — | 228 | 79.6 |
| Ex. 3 | 225 | 81.5 | — | — | 225 | 81.5 |
| Ex. 4 | 225 | 81.5 | — | — | 224 | 81.5 |
| Ex. 5 | 225 | 81.5 | — | — | 224 | 81.5 |
| Comp. Ex. 5 | 225 | 81.5 | — | — | 217 | 76.9 |
| Comp. Ex. 6 | 225 | 81.5 | — | — | 218 | 77.1 |
| Ex. 6 | 228 | 80.8 | — | — | 228 | 80.8 |
| Comp. Ex. 7 | 228 | 80.8 | — | — | 228 | 79.6 |

The entire disclosures of Japanese Patent Application No. 2000-324898 filed on Oct. 25, 2000 and Japanese Patent Application No. 2000-324899 filed on Oct. 25, 2000 including specifications, claims and summaries are incorporated herein by reference in their entireties.

What is claimed is:

1. An olefin oxidation catalyst, comprising:
a carrier, silver and an alkali metal supported thereon, said silver component having been admixed in the form of a complex of silver and an organic compound complexing agent with an alkali metal compound and the carrier prior to processing of the combined materials eventuating in said olefin oxidation catalyst, the olefin oxidation catalyst having an organic substance content of less than 0.1 wt %.

2. An olefin oxidation catalyst comprising:
a carrier, silver and an alkali metal supported thereon, wherein the silver is supported by impregnating the carrier with a solution of an organic complex of silver and heating the impregnated carrier at a temperature ranging from 120 to 500° C. until the content of organic substances becomes less than 0.1 wt %.

3. The olefin oxidation catalyst according to claim 2, wherein the heating of the impregnated carrier is conducted at a temperature ranging from 120 to 250° C.

4. The olefin oxidation catalyst according to claim 2, wherein the heating of the impregnated carrier is conducted at a temperature ranging from 120 to 300° C. under flow of superheated steam.

5. The olefin oxidation catalyst according to claim 2, wherein the carrier having the alkali metal supported thereon is impregnated with the solution of an organic complex of silver.

6. An olefin oxidation catalyst prepared by impregnating a carrier having an alkali metal supported thereon, with an aqueous solution containing an organic amine complex of silver, and heating the impregnated carrier at a temperature ranging from 120 to 500° C. until the content of organic substances becomes less than 0.1 wt %.

7. The olefin oxidation catalyst according to claim 6, wherein cesium and at least one other alkali metal are supported on the carrier.

8. The olefin oxidation catalyst according to claim 6, wherein the heating of the impregnated carrier is conducted at a temperature ranging from 120 to 300° C. under flow of superheated steam.

9. A process for producing an olefin oxidation catalyst comprising a carrier, silver and an alkali metal supported thereon, which comprises impregnating a carrier with a solution of an organic complex of silver and heating the impregnated carrier at a temperature ranging from 120 to 500° C. until the content of organic substances becomes less than 0.1 wt %.

10. The process according to claim 9, wherein the carrier having the alkali metal supported thereon is impregnated with the solution of an organic complex of silver.

11. The olefin oxidation catalyst according to claim 9, wherein the heating of the impregnated carrier is conducted at a temperature ranging from 120 to 300° C. under flow of superheated steam.

12. A process for producing an olefin oxidation catalyst comprising a carrier, and silver and an alkali metal supported thereon, which comprises impregnating a carrier with a solution of an organic complex of silver and heating the impregnated carrier at a temperature of from 120 to 500° C. by permitting it to continuously pass through a heating apparatus and contacting it with a heated gas flowing in the apparatus, until the content of organic substances in the resulting catalyst becomes less than 0.1 wt %, wherein the heating is carried out while replacing a part of the circulating gas with a fresh gas supplied from outside of the system, so that the fresh gas is supplied from outside of the system to the heating apparatus in an amount of at least 10 m$^3$ per kg of the impregnated carrier introduced into the heating apparatus.

13. The process according to claim 12, wherein the carrier having the alkali metal supported thereon is impregnated with the solution of an organic complex of silver.

14. The process according to claim 12, wherein the heating of the impregnated carrier is carried out at a temperature of from 120 to 300° C. by using superheated steam as the heated gas.

15. A process for producing an olefin oxidation catalyst comprising a carrier, and silver and an alkali metal supported thereon, which comprises impregnating a carrier having an alkali metal supported thereon, with an aqueous solution of an organic amine complex of silver and an alkali metal, and heating the impregnated carrier at a temperature of from 120 to 300° C. by permitting it to continuously pass through a heating apparatus in which superheated steam flows, until the content of organic substances in the resulting catalyst becomes less than 0.1 wt %, wherein the heating is carried out while replacing a part of the circulating superheated steam with a fresh superheated steam supplied from outside of the system, so that the fresh superheated steam is supplied from outside of the system to the heating apparatus in an amount of at least 10 m$^3$ per kg of the impregnated carrier introduced into the heating apparatus.

16. The process according to claim 15, wherein a gas flow band type drying apparatus is used as the heating apparatus.

17. A process for producing an olefin oxidation catalyst comprising a carrier, and silver and an alkali metal supported thereon, which comprises impregnating a carrier with a solution of an organic complex of silver, and heating the impregnated carrier at a temperature of from 120 to 500° C. by permitting it to continuously pass through a heating apparatus which comprises a first stage heating zone on an inlet side and a later stage heating zone on an outlet side and until the content of organic substances in the resulting catalyst becomes less than 0.1 wt %, wherein the heating is carried out while, in the later stage heating zone, discharging at least 90% of the supplied gas without circulating it and at the same time, supplying a fresh heated gas from outside of the system.

18. The process according to claim 17, wherein the carrier having the alkali metal supported thereon is impregnated with the solution of an organic complex of silver.

19. The process according to claim 17, wherein the heating of the impregnated carrier is carried out at a temperature of from 120 to 300° C. by using superheated steam as the heated gas.

20. A process for producing an olefin oxidation catalyst comprising a carrier, and silver and an alkali metal supported thereon, which comprises impregnating a carrier having an alkali metal supported thereon, with an aqueous solution containing an organic amine complex of silver and an alkali metal, and heating the impregnated carrier by superheated steam at a temperature of from 120 to 300° C. by permitting it to continuously pass through a gas flow band type drying apparatus, of which the interior is divided into a first stage heating zone on an inlet side and a later stage heating zone on an outlet side by a partition plate, until the content of organic substances in the resulting catalyst becomes less than 0.1 wt %, wherein the heating is carried out while, in the later stage heating zone, discharging at least 90% of the supplied gas without circulating it.

21. The process according to claim 20, wherein the superheated steam discharged from the later stage heating zone is supplied to the first stage heating zone.

* * * * *